United States Patent [19]

Nakayama et al.

[11] 3,939,042

[45] Feb. 17, 1976

[54] PROCESS FOR THE PRODUCTION OF L-GLUTAMIC ACID

[75] Inventors: Kiyoshi Nakayama, Sagamihara; Mamoru Kobata, Kawasaki; Yoshitake Tanaka, Machida; Tadaaki Nomura, Tokyo; Ryoichi Katsumata, Maebashi, all of Japan

[73] Assignee: Kyowa Hakko Kogyo Co., Ltd., Tokyo, Japan

[22] Filed: Aug. 6, 1974

[21] Appl. No.: 495,272

[30] Foreign Application Priority Data

Aug. 11, 1973  Japan................................ 48-89679

[52] U.S. Cl. ...................... 195/49; 195/29; 195/47; 195/79; 195/112
[51] Int. Cl.² ...................... C12D 13/06; C12K 1/02
[58] Field of Search ............. 195/49, 47, 29, 96, 79, 195/46, 112

[56] References Cited
UNITED STATES PATENTS

| | | | |
|---|---|---|---|
| 3,616,224 | 10/1971 | Shiio et al. | 195/49 |
| 3,663,370 | 5/1972 | Kono et al. | 195/49 |
| 3,700,557 | 10/1972 | Nakayama et al. | 195/47 |
| 3,755,082 | 8/1973 | Terui et al. | 195/49 |

OTHER PUBLICATIONS

Nakayama et al., "Induction of Nutritional Mutants of Glutamic Acid Bacteria and Their Amino Acid Accumulation", J. Gen. Appl. Microbiol., Vol. 7, No. 1, (1961), pp. 41–51.
Lehninger, Biochemistry, Worth Publishers, Inc., New York, (1970), pp. 539–566.

*Primary Examiner*—A. Louis Monacell
*Assistant Examiner*—Thomas G. Wiseman
*Attorney, Agent, or Firm*—Fitzpatrick, Cella, Harper & Scinto

[57] ABSTRACT

High yields of L-glutamic acid are produced by culturing mutant strains of microorganisms of the genera Pseudomonas and Protaminobacter in a culture medium containing methanol as the principal source of assimilable carbon. L-glutamic acid is accumulated in the culture liquor and is isolated therefrom.

6 Claims, No Drawings

PROCESS FOR THE PRODUCTION OF L-GLUTAMIC ACID

BACKGROUND OF THE INVENTION

The present invention relates generally to the production of L-glutamic acid by fermentation, and more specifically to the production of L-glutamic acid by culturing a specific mutant strain of microorganism belonging to the genera Pseudomonas and Protaminobacter in a medium containing methanol as the principal carbon source.

L-glutamic acid is an amino acid which is in great and constant demand as a seasoning agent.

Numerous processes have been developed for the production of L-glutamic acid by fermentation using various carbon sources. However, due to the considerable expense attributed to the saccharine carbon sources, processes utilizing microorganisms capable of assimilating less-expensive carbon sources such as hydrocarbons and alcohols have been in considerable demand, particularly those processes and microorganisms which utilize methanol as the principal source of carbon in the culture medium.

L-glutamic acid fermentation from methanol using microorganisms of the genera Pseudomonas and Protaminobacter is known in the art. For example, U.S. Pat. No. 3,663,370 discloses the production of L-glutamic acid from methanol by culturing certain microorganisms belonging to the genus Protaminobacter. Similarly, U.S. Pat. No. 3,616,224 discloses the production of various amino acids including L-glutamic acid by culturing a microorgamism of the genus Pseudomonas in a medium containing methanol as a main carbon source.

Although the processes of the aforesaid United States patents realize the production of acceptable yields of L-glutamic acid, more improved processes which develop higher yields of the product are in demand.

SUMMARY OF THE INVENTION

In accordance with the present invention an improved process has been developed wherein L-glutamic acid is produced in high yields from methanol. The present inventors have obtained various mutants from the known methanol-utilizing microorganisms of the genera Pseudomonas and Protaminobacter, particularly, from those having an ability to produce L-glutamic acid, and examined the productivity of L-glutamic acid by the mutants. As a result, it has been found that a mutant having at least one property selected from: a) a requirement for L-methionine; b) a requirement for L-isoleucine; c) a requirement for L-phenylalanine; and d) a resistance to DL-lysine hydroxamate has a remarkably improved productivity of L-glutamic acid as compared with its parent strain.

DESCRIPTION OF THE INVENTION

In accordance with the present invention, mutants derived from methanol-utilizing, L-glutamic acid-producing microorganisms belonging to the genus Pseudomonas or Protaminobacter having at least one property selected from: a) a requirement for L-methionine; b) a requirement for L-isoleucine; c) a requirement for L-phenylalanine; and d) a resistance to DL-lysine hydroxamate are employed. As used herein the term "a mutant having a requirement" means an auxotrophic mutant including the so-called "leaky" type mutant. A mutant having a "leaky" requirement is also suitable for the present invention.

A mutant suitable for the present invention is derived from a strain which has an ability to utilize methanol and to produce L-glutamic acid and belongs to the genus Pseudomonas or Protaminobacter. An appropriate parent strain is selected by conventional methods known in the art, either from the known strains or from new strains isolated from natural sources.

As for the parent strain's ability to produce L-glutamic acid, there is no critical lower limit. However, it is desirable that the parent strain can produce at least about 100 γ/ml of L-glutamic acid when cultured in a medium, such as disclosed in Example 1 below, under usual culturing conditions for 24 – 48 hours. Examples of particularly suitable parent strains are Pseudomonas insueta ATCC 21276 (disclosed in U.S. Pat. No. 3,616,224), Pseudomonas methanolica ATCC 21704 (disclosed in U.S. Pat. No. 3,755,082) and Protaminobacter thiaminophagus ATCC 21371 (disclosed in U.S. Pat. No. 3,663,370).

A parent strain selected in a manner described above, which is capable of utilizing methanol and of producing L-glutamic acid and belongs to the genus Pseudomonas or Protaminobacter is mutated to obtain mutants having at least one property selected from: a requirement for L-methionine; a requirement for L-isoleucine; a requirement for L-penylalanine; and a resistance to DL-lysine hydroxamate. Such mutants are then suitable for the present invention. Particularly preferred mutants are Pseudomonas insueta K-015 ATCC 21966 (requiring L-methionine), Pseudomonas insueta K-038 ATCC 21967 (requiring L-isoleucine - leaky type), Pseudomonas methanolica LHX-8 ATCC 21968 (resistant to DL-lysine hydroxamate) and Protaminobacter thiaminophagus K-224 ATCC 21969 (requiring L-phenylalanine), which are derived from the above-noted three parent strains. These mutants have been deposited with the American Type Culture Collection, Rockville, Maryland, U.S.A. and are freely available to the public.

In obtaining mutants suitable for the present invention, any of the conventional methods for inducing mutation to obtain a strain having a requirement or a resistance may be employed. For example, such artificial mutation means as X-ray irradiation, ultraviolet ray irradiation, nitrogen mustard treatment, nitrosoguanidine treatment, etc. are appropriate.

More specifically, a mutant having a requirement for L-methionine, L-isoleucine or L-phenylalanine suitable for the present invention may be obtained, for example, in the following manner. Microbial cells of a suitable parent strain are suspended, at a concentration of about $5 \times 10^8$ cells per 1 ml, in tris-maleate buffer solution having a pH of 6 and containing 100 γ/ml of N-methyl-N′-nitro-N-nitrosoguanidine. The suspension is allowed to stand for one hour and then the cells are collected by centrifugation and washed with sterile physiological sodium chloride solution. The cells are then incubated on a nutrient agar plate comprising 20 g/L bouillon powder, 5 g/L yeast extract, 20 ml/L methanol and 20 g/L agar. Cells of resulting colonies are smeared on an agar plate of a minimum medium on which the parent strain can grow and also on a nutrient-supplemented agar plate comprising the minimum medium and an appropriate amount, for example, about 10 mg/L, of a nutrient to be required, i.e., L-methionine, L-isoleucine or L-phenylalanine and then incubated. A strain which does not grow on the minimum medium but grows on the nutrient-supplemented medium, is selected.

In obtaining a mutant having a resistance to DL-lysine hydroxamate, the cells, after treatment with N-methyl-N'-nitro-N-nitrosoguanidine in a manner as described above, are smeared and incubated on an agar plate comprising a minimum medium for the parent strain to which an appropriate amount of DL-lysine hydroxamate is added. The amount of DL-lysine hydroxamate added to the medium should be enough to inhibit growth of the parent strain, and is usually 1 mg/ml. Colonies resulting on the supplemented medium are isolated and, in this manner, a mutant having a resistance to DL-lysine hydroxamate is obtained. In the present invention, usually a mutant having a resistance to 1 mg/ml or more of DL-lysine hydroxamate is suitable.

It will be apparent to those skilled in the art that by repeatedly applying the above described treatments, a mutant having two or more properties can be obtained.

Any culture medium usually used for culturing microorganisms of the genera Pseudomonas and Protaminobacter is suitable for the present invention as long as it contains methanol as a carbon source, a nitrogen source, inorganic materials and other growth promoting factors which may be required by the specific strain employed.

Since high concentrations of methanol will inhibit growth of the microorganism, it is generally desirable that the concentration of methanol in the medium be maintained below about 3 percent (V/V). Good results can be obtained when a medium initially having a low concentration, for example, 0.5–3 percent (V/V) of methanol is used and culturing is carried out while feeding methanol to the medium continuously in an amount of 0.3–0.6 percent by volume based on the volume of the medium per hour, or intermittently in an amount of 0.5–2 percent by volume based on the volume of the medium, as methanol is consumed by the microorganism.

The total amount of methanol consumed may vary depending upon the specific microorganism and culturing conditions, particularly, culturing period. Up to 40 percent (V/V) of methanol based on the volume of the medium may be used when a prolonged culturing period is employed.

As the nitrogen source, ammonium salts such as ammonium chloride, ammonium sulfate, ammonium phosphate and ammonium nitrate, ammonia, and urea may be used. Casamino acid, peptone and yeast extract may also be used as the nitrogen source. The latter natural organic substances contain vitamins, amino acids and other growth-promoting substances and, therefore, are effective to reduce culturing time and to promote production of L-glutamic acid, when supplemented in small amounts to the medium as the nitrogen source. Additionally, as inorganic materials, potassium phosphate, magnesium sulfate, iron and manganese salts may be used.

Mutants of the present invention may require one or more amino acid. When a mutant having the requirement property is used, it is necessary to supplement the amino acid or an appropriate source of the amino acid to the medium as required. In this case, since natural organic substances, such as casamino acid, peptone and yeast extract contain amino acids, when the natural organic substances are used in an appropriate amount as the nitrogen source, the required amino acid or its source may not have to be further supplemented to the medium. Further, when a strain employed has a requirement for a vitamin, for example, a strain of Protaminobacter thiaminophagus which requires thiamine, it is necessary to add the vitamin to the medium.

Culturing is carried out under the aerobic conditions at 20° to 40°C for 2 to 6 days. In order to obtain a high yield of the product, it is desirable that the pH of the medium be maintained at about 4 to 9, preferably, at around neutral during culturing. The pH may preferably be adjusted with ammonia.

After the completion of culturing, the microbial cells are removed from the culture liquor by, for example, filtration. The L-glutamic acid accumulated in the culture liquor is isolated and purified by any of the methods well known in the art, such as an ion exchange resin treatment, crystallization by concentration, or the like.

Practice of specific embodiments of the invention is illustrated by the following representative examples.

EXAMPLE 1

In this example, various strains shown in Table 1 are used. Each of the strains is inoculated into 20 ml of a medium having the following composition in 250 ml-Erlenmeyer flasks.

| | |
|---|---|
| methanol | 20 ml |
| $(NH_4)_2SO_4$ | 10 g |
| $KH_2PO_4$ | 2 g |
| $K_2HPO_4$ | 7 g |
| $MgSO_4.7H_2O$ | 0.5 g |
| $FeSO_4.7H_2O$ | 25 mg |
| $MnSO_4.4H_2O$ | 8 mg |
| thiamine hydrochloride | 1 mg |
| biotin | 10 μg |
| polypeptone | 10 g |
| phenol red | 10 mg |
| water to a volume of 1 L (pH 7.2) | |

Culturing is carried out with shaking at 30°C for 3 days, while feeding 1 percent (V/V) of methanol after 16 hours of culturing and 2 percent (V/V) of methanol after 27 and 40 hours of culturing. During culturing, the pH is adjusted to around neutral with 3N aqueous ammonia three times a day. At the completion of culturing the yield of L-glutamic acid is measured as well as the degree of growth. The results are shown in Table 1 below.

Table 1

| Strains | Growth OD (660 mμ) (×40) | Yield of L-glutamic acid (mg/ml) |
|---|---|---|
| Pseudomonas insueta | | |
| ATCC 21276 (parent) | 0.240 | 1.2 |
| K-015 ATCC 21966 (mutant) | 0.180 | 9.7 |
| K-038 ATCC 21967 (mutant) | 0.150 | 12.9 |
| Pseudomonas methanolica | | |
| ATCC 21704 (parent) | 0.325 | 0.7 |
| LHX-8 ATCC 21968 (mutant) | 0.200 | 7.4 |
| Protaminobacter thiaminophagus | | |
| ATCC 21371 (parent) | 0.316 | 2.1 |
| K-224 ATCC 21969 (mutant) | 0.170 | 11.2 |

From the above table, it is apparent that a yield of L-glutamic acid of 5 – 10 times that obtained by the parent strains is obtained by any of the mutants.

EXAMPLE 2

In this example, Pseudomonas insueta K-038 ATCC 21967 is inoculated into 20 ml of a first seed medium having the following composition in a 250 ml-Erlenmeyer flask.

| | |
|---|---|
| methanol | 20 ml |
| $(NH_4)_2SO_4$ | 5 g |
| $KH_2PO_4$ | 1 g |
| $K_2HPO_4$ | 2.5 g |
| $MgSO_4.7H_2O$ | 0.5 g |
| $FeSO_4.7H_2O$ | 25 mg |
| $MnSO_4.4H_2O$ | 8 mg |
| thiamine hydrochloride | 2 mg |
| biotin | 10 μg |
| polypeptone | 10 g |
| water to a volume of 1 L | |
| (pH 7.2) | |

Culturing is carried out with shaking at 30°C for 27 hours. The first seed culture is then transferred to 300 ml of a second seed medium in a 2 L-Erlenmeyer flask and cultured with shaking at 30°C for 28 hours. The second seed culture is then transferred to 2.7 L of a third seed medium in a 5 L-jar fermenter and cultured with aeration of 3 L/min. and stirring at 600 r.p.m. at 30°C for 24 hours, while maintaining the pH at 6.8 by the addition of concentrated aqueous ammonia. After 20 hours of culturing, 1 percent (V/V) of methanol is fed to the medium. Then 300 ml portions of the thus obtained third seed medium are inoculated into 2.7 L of a main fermentation medium in 5 L-jar fermenters. The second and third seed media and the main fermentation medium have the same composition as that of the first seed medium. Culturing is carried out with aeration of 3 L/min. and stirring at 600 r.p.m. at 30°C for 58 hours while maintaining the pH at 6.8 by the addition of concentrated aqueous ammonia. After 10 hours of fermentation, 0.40–0.55 percent (V/V) per hour of methanol is continuously fed to the medium for a period of 36 hours. As a result, 32.8 mg/ml of L-glutamic acid is produced in the culture liquor while a total of 21.7 percent (V/V) of methanol is used for the fermentation. Then 3 L of the culture liquor is subjected to centrifugation to remove the microbial cells and the filtrate is concentrated and adjusted to pH 3.2 with hydrochloric acid. After crystallization, 75.3 g of L-glutamic acid is obtained.

EXAMPLE 3

In this example, Protaminobacter thiaminophagus K-224 ATCC 21969 is cultured in the same manner as in Example 2 except that the culture medium contains 0.4 g of L-phenylalanine in place of 10 g of polypeptone. After the completion of fermentation, 22.0 mg/ml of L-glutamic acid is produced in the culture liquor while a total of 16.7 percent (V/V) of methanol is used for the fermentation.

What is claimed is:

1. A process for producing L-glutamic acid which comprises culturing a mutant strain derived from a microorganism having an ability to utilize methanol and an ability to produce L-glutamic acid and belonging to a genus selected from Pseudomonas and Protaminobacter, said mutant having at least one property selected from a) a requirement for L-methionine, b) a requirement for L-isoleucine, c) a requirement for L-phenylalanine and d) a resistance to DL-lysine hydroxomate, in a medium containing methanol as the principal carbon source, accumulating L-glutamic acid in the culture liquor and recovering L-glutamic acid therefrom.

2. A process according to claim 1 wherein said mutant strain is selected from the group consisting of Pseudomonas insueta ATCC 21966, Pseudomonas insueta ATCC 21967, Pseudomonas methanolica ATCC 21968 and Protaminobacter thiaminophagus ATCC 21969.

3. A process according to claim 1 wherein said culturing is carried out 20° to 40°C and at approximately neutral pH.

4. A process according to claim 1 wherein said mutant strain is resistant to at least 1 mg/ml of DL-lysine hydroxamate in a culture medium.

5. A process according to claim 1 wherein said methanol is continuously fed to said culture medium.

6. A process according to claim 1 wherein said methanol is intermittently fed to said culture medium.

* * * * *